United States Patent [19]

Brown

[11] 4,013,660
[45] Mar. 22, 1977

[54] INDOLOBENZOXAZEPINES
[75] Inventor: Richard E. Brown, Hanover, N.J.
[73] Assignee: Warner-Lambert Company, Morris Plains, N.J.
[22] Filed: Oct. 30, 1975
[21] Appl. No.: 627,159
[52] U.S. Cl. .............. 260/268 PC; 260/247.5 FP; 260/293.58; 260/326.5 B; 424/250
[51] Int. Cl.² ..................................... C07D 413/14
[58] Field of Search ............................ 260/268 PC
[56] References Cited
UNITED STATES PATENTS 3,813,396  5/1974  Yale et al. .................. 260/268 PC
3,850,942  11/1974  Hester et al. ................ 260/268 PC

FOREIGN PATENTS OR APPLICATIONS 932,494  7/1963  United Kingdom ......... 260/268 TR Primary Examiner—R. Gallagher
Assistant Examiner—Jose Tovar
Attorney, Agent, or Firm—Albert H. Graddis; Frank S. Chow; George M. Yahwak

[57] ABSTRACT

This invention relates to substituted indolobenzoxazepines which show neuroleptic activity.

4 Claims, No Drawings

INDOLOBENZOXAZEPINES

This invention relates to substituted indolobenzoxazepines of the following general formula:

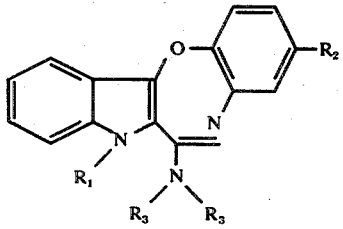

I

In this formula, $R_1$ may be hydrogen, lower alkyl of 1 to 6 carbon atoms or an aralkyl group of 1 to 6 carbon atoms in the chain; $R_2$ may be hydrogen, lower alkyl of 1 to 6 carbon atoms, a trifluoromethyl group or a halogen atom such as chlorine or fluorine and $R_3$ may be hydrogen, lower alkyl of 1 to 6 carbon atoms, a di-lower alkylamino group, or taken together with the nitrogen may form a heterocyclic ring of the formula

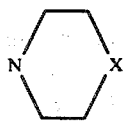

wherein X may be oxygen, sulfur, $-CH_2CH_2-$, a bond connecting the adjacent carbon atoms or $CH-R_4$ or $N-R_4$, wherein $R_4$ may be hydrogen or lower alkyl of 1 to 6 carbon atoms, or $R_3$ may be an ω-aminoalkyl group of the formula

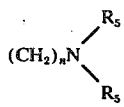

wherein $n$ may be 2 to 4, and $R_5$ may be hydrogen, lower alkyl of 1 to 6 carbon atoms or taken together may form a heterocyclic ring of the formula

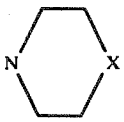

wherein X is as described above.

The compounds of this invention may be prepared using a lactam of the general formula II as starting material. These starting materials are described in our co-pending patent application, U.S. Ser. No. 620,734, filed 8 Oct. 1975. These starting lactams are first treated with a reagent to activate the carbonyl group, and the intermediates thus formed are further treated with the appropriate amine to form the final products of structure I. Among the reagents

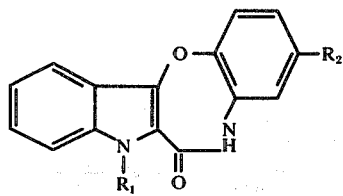

II which may be used to activate the carbonyl group are phosphorous pentachloride and triethyloxonium fluoroborate. The activated intermediates may be isolated but in most cases are conveniently treated, without isolation, with an excess of the appropriate amine. The entire operation is generally carried out in one step using an excess of the amine as solvent. Alternatively, a nonpolar solvent such as benzene or carbon tetrachloride may be used.

In order to further illustrate the subject matter of this invention, I have included the following examples:

EXAMPLE 1

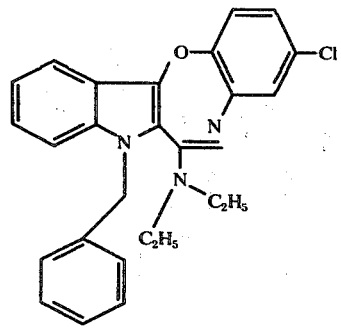

7-benzyl-3-chloro-6(diethylamino)-7H-indolo[3,2-b]-[1,5]benzoxazepine.

A mixture of 7.48g of 3-chloro-7-benzyl-7H-indolo[3,2-b][1,5]benzoxazepine-6(5H)-one and 5.25g of phosphorous pentachloride in 200ml of benzene was stirred at reflux for 4½ hours. A yellow solid precipitated. To this suspension was added at reflux with stirring, 14.6g of diethylamine. The reaction was stirred at reflux for another 2 hours, cooled, diluted with an equal volume of ether, washed twice with $H_2O$, dried and concentrated to an orange oil. The oil crystallized on rubbing with ethanol. Recrystallization for ethanol gave analytical material, mp. 132°–4°.

Anal. Calcd. for $C_{26}H_{24}N_3OCl$: C, 72.63; H, 5.63; N, 9.77; Cl, 8.25. Found: C, 72.50; H, 5.66; N, 9.78; Cl, 8.49.

EXAMPLE 2

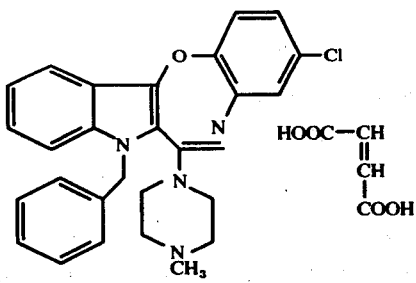

7-benzyl-3-chloro-6-(4-methyl-1-piperazinyl)-7H-indolo[3,2-b][1,5]benzoxazepine fumarate.

In the same way as described in example 1, 3-chloro-7-benzyl-7H-indolo[3,2-b][1,5]benzoxazepine-6(5H)-one, phosphorous pentachloride and N-methyl piperazine were reacted. The product was purified by chromatography on neutral alumina and elution with 3% ethanol in ether. The yellow oil thus obtained was reacted with fumaric acid in hot ethanol and the salt recrystallized from ethanol for analysis, mp. 217°–8°.

Anal. Calcd. for $C_{27}H_{25}N_4OCl.C_4H_4O_4$: C, 64.98; H, 5.10; N, 9.78; Cl, 6.19. Found: C, 64.88; H, 5.14; N, 9.90; Cl, 6.20.

EXAMPLE 3

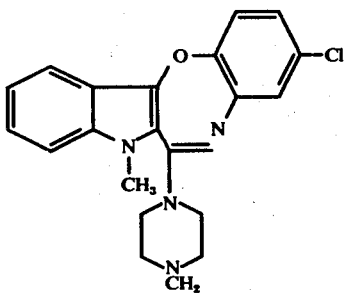

3-chloro-7-methyl-6(4-methyl-1-piperazinyl)-7H-indolo[3,2-b][1,5]benzoxazepine

In the same way as described in example 1, 3-chloro-7-methyl-7H-indolo[3,2-b][1,5]benzoxazepine-6(5H)-one, phosphorous pentachloride and N-methyl piperazine were reacted. The solid product was recrystallized from ethanol for analysis, mp. 187°–8°.

Anal. Calcd. for $C_{21}H_{21}N_4OCl$: C, 66.22; H, 5.56; N, 14.71; Cl, 9.31. Found: C, 65.97; H, 5.57; N, 14.94; Cl, 9.13.

EXAMPLE 4

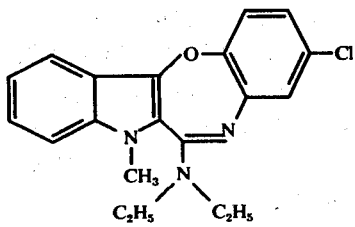

3-chloro-6(diethylamino)-7-methyl-7H-indolo[3,2-b][1,5]benzoxazepine

In the same way as described in example 1, 3-chloro-7-methyl-7H-indolo[3,2-b][1,5]benzoxazepine-6(5H)-one, phosphorous pentachloride and diethylamine were reacted and the solid product recrystallized from methanol for analysis, mp. 127°–8°.

Anal. Calcd. for $C_{20}H_{20}N_3OCl$: C, 67.89; H, 5.70; N, 11.88; Cl, 10.02. Found: C, 68.09; H, 5.77; N, 11.71; Cl, 10.21.

EXAMPLE 5

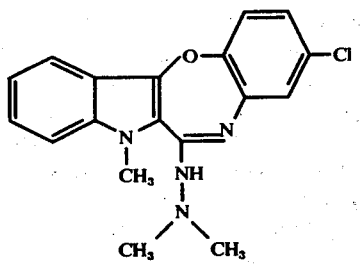

3-chloro-6-(2,2-dimethylhydrazino)-7-methyl-7H-indolo-[3,2-b][1,5] benzoxazepine In the same way as described in example 1, 3-chloro-7-methyl-7H-indolo[3,2-b][1,5]benzoxazepine and dimethylhydrazine were reacted. The crude product was recrystallized from acetonitrile for analysis, mp. 196°–7°.

Anal. Calcd. for $C_{18}H_{17}N_4OCl$: C, 63.44; H, 5.03; N, 16.44; Cl, 10.40. Found: C, 63.43; H, 5.06; N, 16.36; Cl, 10.62.

EXAMPLE 6

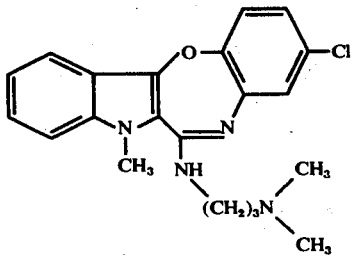

3-chloro-6-{[3-(dimethylamino)propyl]amino}-7-methyl-7H-indolo[3,2-b][1,5]benzoxazepine In the same way as described in example 1, 3-chloro-7-methyl-7H-indolo[3,2-b][1,5]benzoxazepine-6(5H)-one, phosphorous pentachloride and 3-dimethylaminopropylamine were reacted and the crude product recrystallized from acetonitrile for analysis, mp. 156°–7°.

Anal. Calcd. for $C_{21}H_{23}N_4OCl$: C, 65.88; H, 6.06; N, 14.63; Cl, 9.26. Found: C, 65.87; H, 6.17; N, 14.73; Cl, 9.52.

EXAMPLE 7

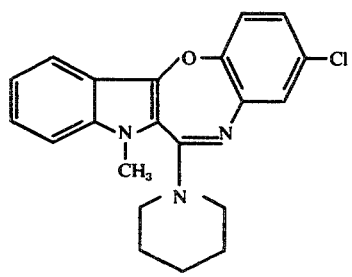

3-chloro-7-methyl-6-piperidino-7H-indolo[3,2-b][1,5]benzoxazepine

A solution of 5.0g of 3-chloro-7-methyl-7H-indolo[3,2-b][1,5]benzoxazepine-6(5H)-one in 60ml of methylene chloride was cooled to 15° and treated with 30ml of a 1N solution of triethyloxonium fluoroborate in methylene chloride. The mixture was stirred for 48 hrs. at ambient temperature. The precipitated solid was filtered, washed with methylene chloride and added to 10ml of piperidine, and the clear solution was heated for 8 hrs. on the steam bath. The mixture was diluted with water, and the precipitated solid was filtered and recrystallized from ethylacetate, mp. 244°-5°.

Anal. Calcd. for $C_{21}H_{20}N_3OCl$: C, 68.94; H, 5.51; N, 11.49; Cl, 9.69. Found: C, 69.02; H, 5.51; N, 11.37; Cl, 9.85.

The compounds of this invention possess CNS depressant properties and as such are valuable as neuroleptic agents; for example, the compound according to structure III is

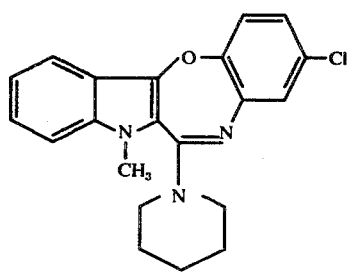

III very active at an intraperitonial dose of 25 mg/kg in calming mice made agressive by isolation (the test procedure of Yen, Stanger and Millman, Arch. Int. Pharmacodyn., 123: 179 (1959)). In addition, the compound of structure IV, when tested according to the procedure of Anden and Stock (J. Pharm. and Pharmacol., 25: 348 (1973)) in subcortical regions of the brain, elevated homovanillic acid levels in the same way as known neuroleptics.

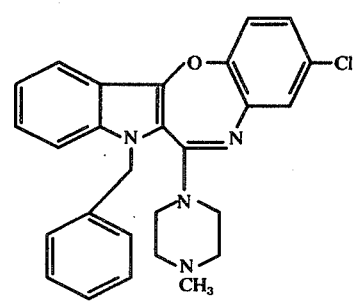

IV

I claim:
1. A compound of the general formula:

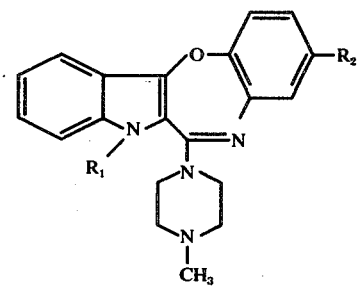

I wherein $R_1$ is:

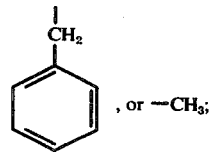, or $-CH_3$;

$R_2$ is -Cl.

2. A compound according to claim 1 wherein $R_1$ is

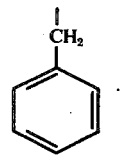

3. The compound according to claim 2 which is 7-benzyl-3-chloro-6-(4-methyl-1-piperazinyl)-7H-indolo[3,2-b][1,5]benzoxazepine fumerate.

4. The compound according to claim 1 which is 3-chloro-7-methyl-6(4-methyl-1-piperazinyl)-7H-indolo[3,2-b][1,5]benzoxazepine.

* * * * *

UNITED STATES PATENT OFFICE
CERTIFICATE OF CORRECTION

PATENT NO. : 4,013,660
DATED : March 22, 1977
INVENTOR(S) : Richard E. Brown

It is certified that error appears in the above-identified patent and that said Letters Patent are hereby corrected as shown below:

Claim 1, line 1, delete "general".

Signed and Sealed this

Seventeenth Day of May 1977

[SEAL]

Attest:

RUTH C. MASON
*Attesting Officer*

C. MARSHALL DANN
*Commissioner of Patents and Trademarks*